United States Patent
Fang et al.

(10) Patent No.: US 10,085,470 B2
(45) Date of Patent: Oct. 2, 2018

(54) **METHOD FOR IMPROVING THE QUALITY OF SOY SAUCE USING *BACILLUS AMYLOLIQUEFACIENS***

(71) Applicants: Fang Fang, Wuxi (CN); Jiran Zhang, Wuxi (CN); Xifei Yang, Wuxi (CN); Chuanwang Hu, Wuxi (CN); Jian Chen, Wuxi (CN); Guocheng Du, Wuxi (CN)

(72) Inventors: Fang Fang, Wuxi (CN); Jiran Zhang, Wuxi (CN); Xifei Yang, Wuxi (CN); Chuanwang Hu, Wuxi (CN); Jian Chen, Wuxi (CN); Guocheng Du, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 102 days.

(21) Appl. No.: 15/204,991

(22) Filed: Jul. 7, 2016

(65) Prior Publication Data

US 2017/0020173 A1    Jan. 26, 2017

(30) Foreign Application Priority Data

Jul. 23, 2015 (CN) .......................... 2015 1 0439604
Dec. 29, 2015 (CN) .......................... 2015 1 1016731

(51) Int. Cl.
*A23L 5/20* (2016.01)
*A23L 27/50* (2016.01)
*A23L 23/00* (2016.01)
*C12N 1/20* (2006.01)
*C12R 1/07* (2006.01)

(52) U.S. Cl.
CPC ................. *A23L 5/28* (2016.08); *A23L 27/50* (2016.08); *C12N 1/20* (2013.01); *C12R 1/07* (2013.01)

(58) Field of Classification Search
CPC . A23L 5/28; A23L 23/00; A23L 27/50; C12N 1/20; C12R 1/07
USPC .......................................................... 426/52
See application file for complete search history.

(56) References Cited

PUBLICATIONS

Cho et al. KR-2015-019435-English Abstract (Year: 2015).*
Matsudo, T. et al. 1993. J. Agric. Food Chem. 41: 352-356 (Year: 1993).*

* cited by examiner

*Primary Examiner* — Hamid R Badr
(74) *Attorney, Agent, or Firm* — Lili Chen

(57) ABSTRACT

The present invention provides a method for improving the quality of soy sauce using *Bacillus amyloliquefaciens*, which relates to the field of microbiology and food technology. The method comprises inoculating *Bacillus amyloliquefaciens* BBE JY06 during soy sauce fermentation. With *Bacillus amyloliquefaciens* addition during soy sauce fermentation, the aroma and tastes of soy sauce is improved and the ethyl carbamate content in soy sauce is decreased as well.

11 Claims, No Drawings

Specification includes a Sequence Listing.

SEQUENCE LISTING

<160> NUMBER OF SEQ ID NOS: 1

<210> SEQ ID NO 1
<211> LENGTH: 1432
<212> TYPE: DNA
<213> ORGANISM: Bacillus amyloliquefaciens

<400> SEQUENCE: 1

```
gcttataatg cagtcgagcg gacagatggg agcttgctcc ctgatgttag cggcggacgg     60
gtgagtaaca cgtgggtaac ctgcctgtaa gactgggata actccgggaa accggggcta    120
ataccggatg gttgtctgaa ccgcatggtt cagacataaa aggtggcttc ggctaccact    180
tacagatgga cccgcggcgc attagctagt tggtgaggta acggctcacc aaggcgacga    240
tgcgtagccg acctgagagg gtgatcggcc acactgggac tgagacacgg cccagactcc    300
tacgggaggc agcagtaggg aatcttccgc aatggacgaa agtctgacgg agcaacgccg    360
cgtgagtgat gaaggttttc ggatcgtaaa gctctgttgt tagggaagaa caagtgccgt    420
tcaaataggg cggcaccttg acggtaccta accagaaagc cacggctaac tacgtgccag    480
cagccgcggt aatacgtagg tggcaagcgt tgtccggaat tattgggcgt aaagggctcg    540
caggcggttt cttaagtctg atgtgaaagc ccccggctca accggggagg gtcattggaa    600 actgggggaac ttgagtgcag aagaggagag tggaattcca cgtgtagcgg tgaaatgcgt    660
agagatgtgg aggaacacca gtggcgaagg cgactctctg gtctgtaact gacgctgagg    720
agcgaaagcg tggggagcga acaggattag ataccctggt agtccacgcc gtaaacgatg    780
agtgctaagt gttaggggggt ttccgcccct tagtgctgca gctaacgcat taagcactcc    840
gcctggggag tacggtcgca agactgaaac tcaaaggaat tgacggggggc ccgcacaagc    900 ggtggagcat gtggtttaat tcgaagcaac gcgaagaacc ttaccaggtc ttgacatcct    960
ctgacaatcc tagagatagg acgtcccctt cgggggcaga gtgacaggtg gtgcatggtt   1020
gtcgtcagct cgtgtcgtga gatgttgggt taagtcccgc aacgagcgca accttgatc    1080 ttagttgcca gcattcagtt gggcactcta aggtgactgc cggtgacaaa ccggaggaag   1140
gtggggatga cgtcaaatca tcatgcccct tatgacctgg gctacacacg tgctacaatg   1200
gacagaacaa agggcagcga aaccgcgagg ttaagccaat cccacaaatc tgttctcagt   1260
tcggatcgca gtctgcaact cgactgcgtg aagctggaat cgctagtaat cgcggatcag   1320
catgccgcgg tgaatacgtt cccgggcctt gtacacaccg cccgtcacac cacgagagtt   1380
tgtaacaccc gaagtcggtg aggtaacctt tatggagcca gccgccgaag gt           1432
```

METHOD FOR IMPROVING THE QUALITY OF SOY SAUCE USING *BACILLUS AMYLOLIQUEFACIENS*

CROSS-REFERENCES AND RELATED APPLICATIONS

This application claims the benefit of priority to Chinese Application No. 201511016731.6, entitled "A method for improving quality of soy sauce using *Bacillus amyloliquefaciens*", filed Dec. 29, 2015, and Chinese Application No. 201510439604.0, entitled "A *Bacillus amyloliquefaciens* strain that utilizes arginine without accumulation of citrulline", filed Jul. 23, 2015, which are herein incorporated by reference in its entirety.

BACKGROUND OF THE INVENTION

Field of the Invention

The present invention relates to the field of microbiology and food technology. In particular, it relates to a method for improving the quality of soy sauce by use of a new *Bacillus amyloliquefaciens* strain.

Description of the Related Art

Aroma and safety are major factors in evaluating soy sauce quality. Currently, methods for enhancing soy sauce aroma has been a hot topic. Higher content of flavor components was realized by adding *Tetragenococcus halophilus* and salt-tolerant yeasts during traditional production process of Chinese soy sauce, while the content of some key indicators of soy sauce including total nitrogen, amino nitrogen, and reducing sugar has not been changed. The amount of total amino acids and flavor components in fish sauce were increased using *Tetragenococcus halophilus* as an initial strain in soy sauce fermentation. However, methods for both enhancing aroma and reducing the content of ethyl carbamate, a reported cancinogen, in soy sauce has so far not been reported.

In recent years, there are increasing attention on food safety, particularly on traditional food and condiment. Ethyl carbamate (EC) has been widely detected in fermentation products. It has been classified as class 2A carcinogen by International Agency for Research on Cancer (IARC) for its potential to induce lung cancer, liver cancer, skin cancer and other kinds of cancers in human. EC has also been widely detected in fermented foods such as wine, rice wine, soy sauce and soybean paste. Researches on the process for producing soy sauce revealed that EC was formed by ethanol (the ethanol content is 2.5% in Japanese soy sauce) reacting with the main precursors, citrulline and urea.

Currently, there is rarely any research on how to control or reduce EC in soy sauce. Some researchers attempted to decrease EC content by reducing the amount of EC precursor, citrulline, by adding *T. halophilus* during soy sauce production. However, it is uncertain whether the final concentration of EC in soy sauce could be lowered or not by adding *T. halophilus*, and its effect on aroma or quality of soy sauce also remains unknown. Other researches on EC reduction were mainly focused on alcohol beverages, which were carried out by adding acidic urease, constructing engineered *Saccharomyces cerevisiae* with low urea production, or adjusting production process.

The precursors to make EC in the soy sauce production are citrulline and ethanol. Decreasing the amount of citrulline in the soy sauce production is therefore an effective way to reduce the EC content in the final product.

In the preproduction of soy sauce, large amount of arginine is generated by hydrolyzing raw materials. The arginine is converted into citrulline by a large class of anaerobic or facultative anaerobic lactic acid bacteria. If the arginine can be used by bacterial strains that have a complete arginine de-iminase pathway that can convert arginine to ornithine, the accumulation of citrulline in soy sauce can be reduced.

The goal of present invention is to provide a new salt-resistant *Bacillus amyloliquefaciens* strain that can effectively convert arginine to ornithine without accumulation of citrulline under high salt conditions and can be used to reduce the EC content in soy sauce. In addition, it is found that the new strain not only can reduce the EC content, but also can enhance the aroma and taste of the soy sauce product.

DETAILED DESCRIPTION

The present invention provides a new *Bacillus amyloliquefaciens* strain, *Bacillus amyloliquefaciens* BBE JY06, that can effectively convert arginine into ornithine without accumulation of citrulline under high salt conditions. Secondly, the present invention provides a method to reduce the EC content in soy sauce by adding *Bacillus amyloliquefaciens* BBE JY06 in the production process. Thirdly, the present invention provides a method for both improving the flavor and taste of soy sauce and reducing the EC content by use of *Bacillus amyloliquefaciens* BBE JY06 in the production process of soy sauce. As an added benefit, *Bacillus amyloliquefaciens* is a safe food-grade bacterial strain.

The first goal of the present invention is to provide a new *Bacillus amyloliquefaciens* strain, *Bacillus amyloliquefaciens* BBE JY06, that can effectively convert arginine into ornithine without accumulation of citrulline under high salt conditions.

The new *Bacillus amyloliquefaciens* strain having the desired property of converting arginine into ornithine without accumulation of citrulline is isolated from Japanese soy sauce moromi mash. Bromocresol purple-based amino acid assay culture medium is used to screen for a *Bacillus amyloliquefaciens* strain that is good at converting arginine to ornithine. Bromocresol purple is a pH indicator that turns into a purplish color when arginine is converted into ornithine which has a basic pH. By comparing the 16S rDNA sequence of the newly isolated bacterial strain with known sequences in the NCBI database, it was confirmed that the new bacterial strain is a *Bacillus amyloliquefaciens*. The new strain, named *Bacillus amyloliquefaciens* BBE JY06, was conserved in China Center for Type Culture Collection in Wuhan University, Wuhan, Hubei, China on Jul. 2, 2015 with the code of CCTCC NO.: M 2015423. The 16S rDNA sequence is shown in SEQ ID NO:1.

The second goal of the present invention is to provide a method for reducing the content of ethyl carbamate in soy sauce by use of *Bacillus amyloliquefaciens* BBE JY06.

The method is performed by inoculating *Bacillus amyloliquefaciens* BBE JY06 during soy sauce fermentation.

In one embodiment of the invention, the *Bacillus amyloliquefaciens* BBE JY06 is inoculated to the soy sauce fermentation mash on the 0 to $3^{rd}$ day from the beginning of the fermentation after mixing the koji and brine together, and the final concentration of *Bacillus amyloliquefaciens* BBE JY06 inoculated in the fermentation mash is $1\times10^7 \sim 1\times10^8$ CFU·mL$^{-1}$.

In one embodiment, the method comprises the following steps: (1) koji preparation: defatted soybean and parched and crushed wheat are mixed, soaked, sterilized and cooled; bran and wheat flour are added to the cooled mixture, and *Aspergillus oryzae* spore is inoculated into the cooled mixture to make a starter koji; when koji color turned greenish yellow, mature koji is obtained; (2) soy sauce fermentation: mature koji and brine are mixed together and the fermentation begins (the first day of fermentation); *Bacillus amyloliquefaciens* BBE JY06 is inoculated on the 0~$3^{rd}$ day of the fermentation process and initially cultivated at 10~20°

C. for 23 days; *Torulopsis glabrata* and *Zygosaccharomyces rouxii* are inoculated at an amount of $1\times10^7$ CFU·mL$^{-1}$ on the seventh and fourteenth day of the fermentation, respectively. The fermentation temperature gradually increases from the initial cultivation temperature to 30° C. from 23$^{rd}$ to 30$^{th}$ day, reaching 30° C. on the 30th day, and is kept at 30° C. for the remaining period of the fermentation. The fermentation process lasts a total of 90 days.

The third goal of the present invention is to provide a method for both enhancing aroma and reducing the EC content of soy sauce by use of *Bacillus amyloliquefaciens* BBE JY06 in the production process of soy sauce.

The method comprises inoculating *Bacillus amyloliquefaciens* BBE JY06 during soy sauce fermentation.

In one embodiment of the invention, the *Bacillus amyloliquefaciens* BBE JY06 is inoculated to the soy sauce fermentation mash at a final concentration of $1\times10^7\sim1\times10^8$ CFU·mL$^{-1}$.

In one embodiment of the invention, the *Bacillus amyloliquefaciens* BBE JY06 is inoculated to the soy sauce fermentation mash at a final concentration of $1\times10^7$ CFU·mL$^{-1}$.

In one embodiment of the invention, the *Bacillus amyloliquefaciens* BBE JY06 is inoculated to the soy sauce fermentation mash at a final concentration of $1\times10^8$ CFU·mL$^{-1}$.

In one embodiment of the invention, the *Bacillus amyloliquefaciens* BBE JY06 is inoculated on the 0~3$^{rd}$ day from the beginning of the fermentation when mixing the koji and brine together.

In one embodiment, the method comprises the following steps: (1) koji preparation: defatted soybean and the parched and crushed wheat are mixed, soaked, sterilized and cooled; bran and wheat flour are added to the cooled mixture to make a starter koji, and *Aspergillus oryzae* spore is inoculated into the starter koji; when the color of the koji turns greenish yellow, mature koji is obtained; (2) soy sauce fermentation: the mature koji and brine are mixed together and the fermentation begins; *Bacillus amyloliquefaciens* BBE JY06 is inoculated into the fermentation mixture on the 0~3$^{rd}$ day from the beginning of the fermentation and the fermentation is performed at 10~20° C. for 23 days; *Torulopsis glabrata* and *Zygosaccharomyces rouxii* are inoculated at a concentration of $1\times10^7$ CFU·mL$^{-1}$ on the seventh and fourteenth day of the fermentation, respectively. The fermentation temperature gradually increases from the initial cultivation temperature to 30° C. from the 23$^{rd}$ to the 30$^{th}$ day, reaching 30° C. on the 30th day, and is kept at 30° C. for the remaining period of the fermentation. The fermentation process lasts a total of 90 days.

The present invention provides a method for improving the quality of soy sauce by using *Bacillus amyloliquefaciens* BBE JY06 in the production process. The *Bacillus amyloliquefaciens* BBE JY06 is good at degrading arginine but not accumulating citrulline under high salt conditions. Using *Bacillus amyloliquefaciens* BBE JY06 in soy sauce fermentation leads to less citrulline accumulation and less ethyl carbamate formation. With an addition of the *Bacillus amyloliquefaciens* during soy sauce fermentation, the aroma and tastes of soy sauce is improved, and at the same time EC content is decreased. As an added benefit, *Bacillus amyloliquefaciens* BBE JY06 is a safe food-grade bacterial strain.

EXAMPLES

Materials and Methods

Amino acid assay medium: yeast extract 5 g/L, beef extract 5 g/L, tryptone 5 g/L, NaCl 180 g/L, glucose, 0.5 g/L, Tween-80 1 g/L, MgSO$_4$.7H$_2$O 0.2 g/L, MnSO$_4$.H$_2$O 0.05 g/L, FeSO$_4$.4 g/L, citric acid triamide 2 g/L, CaCO$_3$.1 g/L, pyridoxal-5-phosphate 0.05 g/L, K$_2$HPO$_4$.2 g/L, pH 6.0. When it is used to detect a particular amino acid, add 10 g/L of the amino acid to be detected to the culture medium.

*Bacillus amyloliquefaciens* separation plate: add 10 g/L arginine, 0.06 g/L Bromocresol purple to the amino acid assay medium above to make agar plates. Culture condition: 30° C., 5 days.

Genomic DNA extraction kit: E.Z.N.A Bacterial DNA Kit D3350-01 (Omega Bio-tek, Inc., Norcross, Ga., USA)

Cultivation of *Bacillus amyloliquefaciens*: *Bacillus amyloliquefaciens* BBE JY06 was streaked and cultured on LB agar plate containing 100 g·L$^{-1}$ NaCl and cultivated at 30° C. for 2 days; colonies were picked and cultured statically in a LB medium containing 100 g·L$^{-1}$ NaCl at 30° C. for 36 hours; cells were obtained by centrifugation at 8000 r·min$^{-1}$ under 4° C. for 1 mm, and then resuspended in a phosphate buffer solution (PBS, pH 7.0) at a volume ratio of 1:5 (original LB medium vs. resuspended PBS).

Example 1. *Bacillus amyloliquefaciens* Screening Method

A sample was taken from Japanese soy sauce moromi mash on the 21$^{st}$ day of the fermentation, and was diluted and plated onto a *Bacillus amyloliquefaciens* separation plate containing 10 g/L arginine and 0.06 g/L Bromocresol purple, which was cultured for 5 days at 30° C. Single colonies that had a rough surface, an opaque color, a raised and irregular shape, and a large reddish purple circle around it, were selected and streaked onto a LB agar plate containing 100 g/L NaCl to culture for pure colonies. Two days later, the cultured colonies were inoculated into a liquid LB medium with 100 g/L NaCl and cultured for 36 hours. The DNA of the bacteria were extracted using E.Z.N.A Bacterial DNA Kit D3350-01. By comparing the 16S rDNA of the isolated bacteria with known sequences in NCBI database, it was confirmed that a *Bacillus amyloliquefaciens* strain was obtained. The new strain, named *Bacillus amyloliquefaciens* BBE JY06, was conserved in China Center for Type Culture Collection in Wuhan University, Wuhan, Hubei, China on Jul. 2, 2015 with the code of CCTCC NO.: M 2015423. The 16S rDNA sequence of *Bacillus amyloliquefaciens* BBE JY06 is shown in SEQ ID NO:1.

Example 2. Analysis of Arginine Utilizing Ability of *Bacillus amyloliquefaciens* BBE JY06

The activated *Bacillus amyloliquefaciens* BBE JY06 colony was inoculated in LB medium containing 100 g·L$^{-1}$ NaCl, cultivated at 30° C. for 36 hours; cells were obtained by centrifugating 5 mL culture medium at 8000 r·min$^{-1}$ under 4° C. for 1 mm, and then resuspended in 1 mL PBS (pH 7.0).

500 µL *Bacillus amyloliquefaciens* suspension was inoculated to a 5 mL tube with 4 mL amino acid assay medium, which contained 10 g U' arginine, and the OD$_{600}$ was 7.8 after inoculation. Static cultivation was performed at 30° C. for 3 days. Content of arginine, citrulline and ornithine were determined by HPLC. Results in Table 1 showed that, after three days of cultivation, arginine and citrulline was not detected while ornithine was accumulated, indicating that the *Bacillus amyloliquefaciens* could convert arginine into ornithine without citrulline accumulation.

TABLE 1

Content of arginine, citrulline and ornithine under high-salt cultivation

| | ΔArg (g·L$^{-1}$) | ΔCit (g·L$^{-1}$) | ΔOrn (g·L$^{-1}$) | Molar conversion rate (%) |
|---|---|---|---|---|
| 180 g·L$^{-1}$ NaCl | 10.00 | 0 | 6.31 | 83.20 |

ΔArg (g·L$^{-1}$): Arginine consumption;
ΔCit (g·L$^{-1}$): Citrulline generation;
ΔOrn (g·L$^{-1}$): Ornithine generation.

Example 3. Soy Sauce Production

Soy sauce production was carried out as follows:

(1) koji preparation: defatted soybean and the parched and crushed wheat were mixed, soaked for 8 h, sterilized at 121° C. for 5 mm and cooled to 80° C.; bran and wheat flour were added to the cooled mixture, and the mass ratio of defatted soybean, the parched and crushed wheat, bran, wheat flour was 20:15:1:1; Aspergillus oryzae spore was inoculated into the mixture at a ratio of 8×10$^9$ CFU·g$^{-1}$ relative to the total mass of original material (the original material was the material used for mature koji fermentation, including defatted soybean, the parched and crushed wheat, bran, wheat flour and water); the resulting mixture was cultivated at 30° C. for 46~48 hours and overturned every 6~8 hours; when the koji color turned greenish yellow, mature koji was obtained.

(2) soy sauce fermentation: mature koji and 20% brine (w/v) were mixed together according to a volume ratio of 1:1:7 and the fermentation began; Bacillus amyloliquefaciens BBE-JY06 was inoculated on the 0~3$^{rd}$ day from the beginning of the fermentation process and cultivated at 10~20° C.; Torulopsis glabrata and Zygosaccharomyces rouxii were inoculated at an amount of 1×10$^7$ CFU·mL$^{-1}$ on the seventh and fourteenth day of the fermentation, respectively; the whole fermentation process lasted 90 days at 30° C.

After the fermentation process finished, physical and chemical indicators in soy sauce including content of EC and EC precursors, were determined, sensory characteristics of the obtained soy sauce was evaluated. Data were shown in Table 2 to Table 5.

Results in Table 2 showed that the main physical and chemical indicators of soy sauce were little affected by the addition of Bacillus amyloliquefaciens BBE-JY06 during soy sauce fermentation while the total amount of acids were increased. The main component of the acids was lactic acid, which is a flavor component that could react with ethanol by esterification reaction to produce ethyl lactate, resulting in improved soy sauce aroma.

TABLE 2

Physical and chemical indicators of the soy sauce

| Soy sauce samples | Total acid g/100 mL | Amino nitrogen g/100 mL | Salts g/100 mL |
|---|---|---|---|
| 1 | 1.741 | 1.371 | 16.730 |
| 2 | 2.126 | 1.262 | 16.420 |
| 3 | 2.253 | 1.356 | 16.710 |
| 4 | 1.928 | 1.306 | 16.450 |

Note:
1, without BBE-JY06 addition;
2, 1 × 10$^7$ CFU·mL$^{-1}$ BBE-JY06 was added at the beginning of the fermentation;
3, 1 × 10$^8$ CFU·mL$^{-1}$ BBE-JY06 was added at the beginning of the fermentation;
4, 1 × 10$^7$ CFU·mL$^{-1}$ BBE-JY06 was added on the 3$^{rd}$ day of the fermentation.

According to Table 3, the addition amount of Bacillus amyloliquefaciens BBE-JY06 could not be less than 1×10$^7$ CFU·mL$^{-1}$ in soy sauce fermentation. In addition, adding Bacillus amyloliquefaciens on the 3$^{rd}$ day of fermentation could improve soy sauce aroma.

TABLE 3

Sensory evaluation of soy sauce

| Samples | Aroma | Score (0~20) | Taste | Score (0~20) | Color and luster | Score (0~10) | Characteristics | Score (0~10) | Total score |
|---|---|---|---|---|---|---|---|---|---|
| 1 | A rich sauce flavor and ethanol fragrant, no bad smell | 17 | delicious and mellow, salt and sweet is balanced, a strong aftertaste, a bit acerbity taste | 18 | Reddish-brown, shiny | 9 | Bright and gloss | 10 | 54 |
| 2 | Sauce aroma, no bad smell | 15 | Fresh but single taste, salty prominent | 15 | Brownish orange, shiny | 8 | Less clear | 8 | 46 |
| 3 | A rich sauce flavor and ethanol fragrant, no bad smell | 17 | Outstanding fresh and sweet, salt and sweet is balanced | 16 | Brownish orange, shiny | 8 | Clear, no suspended matter or impurities | 9 | 50 |
| 4 | A rich sauce flavor, alcohols aroma and esters fragrant; no bad smell | 18 | delicious and mellow, salt and sweet is balanced, a strong aftertaste | 19 | Reddish-brown, shiny | 9 | Bright and gloss | 10 | 56 |

Note:
1, without BBE-JY06 addition;
2, 1 × 10$^7$ CFU·mL$^{-1}$ BBE-JY06 was added at the beginning of the fermentation;
3, 1 × 10$^8$ CFU·mL$^{-1}$ BBE-JY06 was added at the beginning of the fermentation;
4, 1 × 10$^7$ CFU·mL$^{-1}$ BBE-JY06 was added on the 3$^{rd}$ day of the fermentation.

According to Table 4, *Bacillus amyloliquefaciens* BBE-JY06 addition during soy sauce fermentation could lead to less accumulation of the EC precursor, citrulline, which results in reduced EC content in soy sauce products. In addition, it was found that the EC reduction by adding *Bacillus amyloliquefaciens* on the 3$^{rd}$ day was 50%, which was not as effective as adding *Bacillus amyloliquefaciens* at the beginning of the fermentation.

TABLE 4

Concentrations of EC and its precursors

| Samples | Urea (mg · L$^{-1}$) | Citrulline (g · L$^{-1}$) | EC content before sterilization (ppb) | EC content after sterilization (ppb) |
|---|---|---|---|---|
| 1 | 8.60 | 4.70 | 9 | 41 |
| 2 | 6.20 | 1.00 | — | 12 |
| 3 | 6.50 | 0.90 | — | 7 |
| 4 | 6.50 | 1.50 | — | 21 |

Note:
"—", not detected;
1, without BBE-JY06 addition;
2, 1 × 10$^7$ CFU · mL$^{-1}$ BBE-JY06 was added at the beginning of the fermentation;
3, 1 × 10$^8$ CFU · mL$^{-1}$ BBE-JY06 was added at the beginning of the fermentation;
4, 1 × 10$^7$ CFU · mL$^{-1}$ BBE-JY06 was added on the 3$^{rd}$ day of the fermentation.

As it can been seen from Table 2 to Table 5, *Bacillus amyloliquefaciens* BBE-JY06 could convert most arginine to ornithine with an amount of 1×10$^7$~1×10$^8$ CFU·mL$^{-1}$ added on the 0~3$^{rd}$ day of soy sauce fermentation. Although the EC reduction in soy sauce with *Bacillus amyloliquefaciens* BBE-JY06 on the 3$^{rd}$ day of fermentation was not as effective as the EC reduction with the addition at the beginning of the soy sauce fermentation, adding *Bacillus amyloliquefaciens* BBE-JY06 on the 3$^{rd}$ day of fermentation could improve the soy sauce aroma.

TABLE 5

Content of arginine, citrulline and ornithine in raw soy sauce

| Samples | Arginine (g · L$^{-1}$) | Citrulline (g · L$^{-1}$) | Ornithine (g · L$^{-1}$) |
|---|---|---|---|
| 1 | 1.26 | 4.70 | 1.05 |
| 2 | 0.81 | 1.00 | 4.52 |
| 3 | 0.74 | 0.90 | 4.80 |
| 4 | 0.83 | 1.50 | 4.31 |

Note:
1, without BBE-JY06 addition;
2, 1 × 10$^7$ CFU · mL$^{-1}$ BBE-JY06 was added at the beginning of the fermentation;
3, 1 × 10$^8$ CFU · mL$^{-1}$ BBE-JY06 was added at the beginning of the fermentation;
4, 1 × 10$^7$ CFU · mL$^{-1}$ BBE-JY06 was added on the 3$^{rd}$ day of the fermentation.

Example 4. Application of *Bacillus amyloliquefaciens* BBE-JY06 Increases the Amount of γ-Polyglutamic Acid in Soy Sauce (1) *Bacillus amyloliquefaciens* BBE-JY06 Cultivated in Normal Medium Seed medium: Sucrose 1%, peptone 1%, L-glutamic acid 2%, MgSO$_4$.1%, NaCl 0.5%, K$_2$HPO$_4$.05%, adjusted to pH 7.0, sterilized at 115° C. for 20 min.

Fermentation medium: Sucrose 2%, peptone 2%, L-glutamic acid 2%, MgSO$_4$.1%, NaCl 2%, K$_2$HPO$_4$.05%, adjusted to pH 7.0, sterilized at 115° C. for 20 min.

*Bacillus amyloliquefaciens* BBE-JY06 was inoculated in a seed medium, cultivated at 200 r·min$^{-1}$ for 12 hours. It was then transferred into a 250 mL flask containing 50 mL fermentation medium with an inoculation volume of 10%, and statically cultivated at 37° C. for 24 hours.

(2) *Bacillus amyloliquefaciens* BBE-JY06 Cultivated in Soy Sauce Fermentation

The *Bacillus amyloliquefaciens* BBE-JY06 was cultivated by the method described in Example 3. The resulting soy sauce sample was the same as sample No. 2 of Example 3.

(3) Determination of γ-Polyglutamic Acid 50 mL fermentation broth or culture medium was centrifuged at 9000 r·min$^{-1}$ for 15 min. The supernatant was collected and was adjusted to pH 4 by HCl. The supernatant was mixed with 4 volumes of methanol and incubated at 4° C. overnight. The mixture was centrifuged at 8000 r·min$^{-1}$ for 15 min to collect the precipitate. The obtained precipitate was washed with 2 volumes of methanol, and then dissolved in ultrapure water and dialyzed for 16 hours. 4 volumes of methanol was added to the dialysis solution, and the solution was centrifuged to collect the precipitate. The precipitate was dissolved in ultrapure water, and freeze-dried for 48 hours to collect the resulting powder. Light yellow powder was obtained and dissolved by 6 mol·L$^{-1}$ HCl. It was then vacuum-treated and incubated in boiling water for 24 hours. The resulting γ-polyglutamic acid solution obtained by acid hydrolysis was cooled and centrifuged at 1000 r·min$^{-1}$ for 5 min. The black impurities were discarded, and the pH of the γ-polyglutamic acid solution was adjusted to neutral by adding NaOH. Then, the solution was diluted 5 times, 10 times and 15 times with pure water, respectively. 1 mL diluted sample was filtered and the γ-polyglutamic acid content of the diluted sample was measured by HPLC. 0.2 g·L$^{-1}$ γ-polyglutamic acid solution was used as the standard sample, and the sample without acid hydrolysis was used as the control.

γ-polyglutamic acid is one of a water-soluble poly amino acids produced by microbial fermentation. It plays a role as a health factor in food for promoting minerals absorptions. As it is shown in Table 6, *Bacillus amyloliquefaciens* BBE-JY06 either added in soy sauce fermentation process or cultivated alone could produce γ-polyglutamic acid or increase the content of γ-polyglutamic acid. The content of γ-polyglutamic acid in soy sauce with *Bacillus amyloliquefaciens* BBE-JY06 addition increased 64% than that in control group (comparing sample 3 vs. 2 in Table 6).

TABLE 6

Content of γ-polyglutamic acid in fermentation or culture medium

| Samples | γ-polyglutamic acid (g · L$^{-1}$) |
|---|---|
| 1 | 0.505 |
| 2 | 1.038 |
| 3 | 1.703 |

Notes:
1, BBE-JY06 cultivated in fermentation medium;
2, soy sauce without BBE-JY06 addition;
3, soy sauce with 1 × 10$^7$ CFU · mL$^{-1}$ BBE-JY06 added at the beginning of the fermentation.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for producing soy sauce, comprising addition of appropriate amount of *Bacillus amyloliquefaciens* BBE JY06 (CCTCC NO. M2015423) during soy sauce fermentation, wherein the soy sauce made with said *Bacillus amyloliquefaciens* BBE JY06 contains less ethyl carbamate than that made without said *Bacillus amyloliquefaciens* BBE JY06.

2. The method of claim 1, wherein said *Bacillus amyloliquefaciens* BBE JY06 is inoculated to a soy sauce fermentation mash at an amount of $1\times10^7$~$1\times10^8$ CFU·mL$^{-1}$.

3. The method of claim 2, wherein said *Bacillus amyloliquefaciens* BBE JY06 is inoculated to said soy sauce fermentation mash at an amount of $1\times10^7$ CFU·mL$^{-1}$.

4. The method of claim 2, wherein said *Bacillus amyloliquefaciens* BBE JY06 is inoculated to said soy sauce fermentation mash at an amount of $1\times10^8$ CFU·mL$^{-1}$.

5. The method of claim 1, comprising inoculating said *Bacillus amyloliquefaciens* BBE JY06 on the 0~3$^{rd}$ day from the beginning of the fermentation of soy sauce.

6. The method of claim 1, comprising the steps of:

1) koji preparation: defatted soybean and parched and crushed wheat are mixed, soaked, sterilized and then cooled; bran and wheat flour are added to the cooled mixture, and *Aspergillus oryzae* spore is inoculated in the mixture at the same time; when koji color turns greenish yellow, mature koji is obtained; and 2) soy sauce fermentation: mature koji and brine are mixed together and the fermentation begins; *Bacillus amyloliquefaciens* BBE JY06 is inoculated on the 0~3$^{rd}$ day from the beginning of the fermentation process and cultivated at 10~20° C.; *Torulopsis glabrata* and *Zygosaccharomyces rouxii* are inoculated at an amount of $1 \times 10^7$ CFU·mL$^{-1}$ on the seventh and fourteenth day of the fermentation, respectively; the whole fermentation process lasts 90 days.

7. The method of claim 6, wherein said soy sauce fermentation is initially cultivated at 10-20° C. for 23 days and the temperature is gradually increased to 30° C. from the 23$^{rd}$ to the 30$^{th}$ day.

8. A method for reducing the content of ethyl carbamate in soy sauce, comprising inoculating *Bacillus amyloliquefaciens* BBE JY06 during soy sauce fermentation.

9. The method of claim 8, wherein the *Bacillus amyloliquefaciens* BBE JY06 is inoculated to soy sauce fermentation mash on the 0 to 3$^{rd}$ day from the beginning of the fermentation after mixing a koji and brine together, and wherein the amount of *Bacillus amyloliquefaciens* BBE JY06 is $1 \times 10^7 \sim 1 \times 10^8$ CFU·mL$^{-1}$.

10. The method of claim 8, comprising the steps of:
1) koji preparation: defatted soybean and parched and crushed wheat are mixed, soaked, sterilized and cooled; bran and wheat flour are added to the cooled mixture, and *Aspergillus oryzae* spore is inoculated into the mixture at the same time; when koji color turns greenish yellow, mature koji is obtained; and
2) soy sauce fermentation: mature koji and brine are mixed together and the fermentation begins; *Bacillus amyloliquefaciens* BBE JY06 is inoculated into the fermentation mixture on the 0~3$^{rd}$ day from the beginning of the fermentation and cultivated at 10~20° C.; *Torulopsis glabrata* and *Zygosaccharomyces rouxii* are inoculated at an amount of $1 \times 10^7$ CFU·mL$^{-1}$ on the seventh and fourteenth day of the fermentation, respectively; the whole fermentation process lasts 90 days.

11. The method of claim 10, wherein said soy sauce fermentation is initially cultivated at 10-20° C. for 23 days and the temperature is gradually increased to 30° C. from the 23$^{rd}$ to the 30$^{th}$ day.

* * * * *